US007340957B2

(12) United States Patent
Kaduchak et al.

(10) Patent No.: US 7,340,957 B2
(45) Date of Patent: Mar. 11, 2008

(54) ULTRASONIC ANALYTE CONCENTRATION AND APPLICATION IN FLOW CYTOMETRY

(75) Inventors: Gregory Kaduchak, Los Alamos, NM (US); Greg Goddard, Los Alamos, NM (US); Gary Salzman, White Rock, NM (US); Dipen Sinha, Los Alamos, NM (US); John C. Martin, Los Alamos, NM (US); Christopher Kwiatkowski, Los Alamos, NM (US); Steven Graves, San Juan Pueblo, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 143 days.

(21) Appl. No.: 10/979,065

(22) Filed: Nov. 2, 2004

(65) Prior Publication Data

US 2006/0021437 A1 Feb. 2, 2006

Related U.S. Application Data

(60) Provisional application No. 60/592,169, filed on Jul. 29, 2004.

(51) Int. Cl.
*G01H 17/00* (2006.01)
*G01N 15/06* (2006.01)

(52) U.S. Cl. .................................... 73/570.5
(58) Field of Classification Search ............ 73/570.5
See application file for complete search history.

(56) References Cited

U.S. PATENT DOCUMENTS 4,523,682 A * 6/1985 Barmatz et al. ............ 209/638
4,523,982 A * 6/1985 Lee ............................. 522/21
5,831,166 A * 11/1998 Kozuka et al. ............... 73/570
6,003,388 A * 12/1999 Oeftering ................. 73/864.01
6,216,538 B1 * 4/2001 Yasuda et al. ............. 73/570.5
6,449,563 B1 * 9/2002 Dukhin et al. ............... 702/22
2004/0139792 A1 * 7/2004 Cobb ........................ 73/61.75

FOREIGN PATENT DOCUMENTS

| JP | 63139231 A | * | 6/1988 |
| JP | 06241977 A | * | 9/1994 |
| JP | 08266891 A | * | 10/1996 |

OTHER PUBLICATIONS

King, L. V., "On the acoustic radiation on spheres," *Proc. R. Soc. A.*, 147, 212-240, (1933).

(Continued)

*Primary Examiner*—Hezron Williams
*Assistant Examiner*—Rose M. Miller
(74) *Attorney, Agent, or Firm*—Mark N. Fitzgerald

(57) ABSTRACT

The present invention includes an apparatus and corresponding method for concentrating analytes within a fluid flowing through a tube using acoustic radiation pressure. The apparatus includes a function generator that outputs a radio frequency electrical signal to a transducer that transforms the radio frequency electric signal to an acoustic signal and couples the acoustic signal to the tube. The acoustic signal is converted within the tube to acoustic pressure that concentrates the analytes within the fluid.

26 Claims, 17 Drawing Sheets

OTHER PUBLICATIONS

L. P. Gorkov, "On the forces acting on a small particle in an acoustical field in and ideal fluid", *Soviet Physics-Doklady*,6, 773-775 (1962).

R. K. Gould, W. T. Coakley, "The effects of acoustic forces on small particles in suspension", in *Proceedings of the 1973 Symposium on Finite Amplitude Wave Effects in Fluids*, edited by L. Bjorno, Pergamon, Guildford, 1974, pp. 252-257.

K. Higashitani, M. Fukushima, Y, Matsuno, "Migration of suspended particles in plane stationary ultrasonic field", *Chem. Eng. Sci.* 36, 1187-1192 (1981).

D. C. Ricks, H. Schmidt, "A numerically stable global matrix method for cylindrically layered shells excited by ring forces," *J. Acoust. Soc. Am.* 95, 3339-3349 (1994).

* cited by examiner

ULTRASONIC ANALYTE CONCENTRATION AND APPLICATION IN FLOW CYTOMETRY

RELATED APPLICATIONS

This application claims the benefit of provisional application No. 60/592,169 filed on Jul. 29, 2004, titled "Ultrasonic Analyte Concentration and Application in Flow Cytometry".

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to the use of ultrasonic energy, and, more particularly, to the use of ultrasonic energy to concentrate analytes within a fluid.

BACKGROUND OF THE INVENTION

The term "analyte" is used throughout the body of this text and is defined as a particle that is of interest to the user of the present invention. The term "particle" is defined as a very small unit of matter, to include but not limited to: biological cells, cell organelles, organic/inorganic molecules, and microspheres.

The use of acoustic standing waves to concentrate homogeneously suspended particles in a fluid at acoustic pressure nodal or antinodal planes within the fluid was first described by A. Kundt, and O. Lehmann, "Longitudinal vibrations and acoustic figures in cylindrical columns of liquids", *Annalen der Physik und Chemie (Poggendorf's Annalen)*, 153, 1-11 (1874). However, the inclusion of suspended particles was used only to enhance the visualization of the ultrasonic waves Kundt and Lehmann sought to describe.

Acoustic forces may be used to non-invasively position, concentrate, or fractionate particles in a fluid. Particles suspended within a fluid filled cavity subject to ultrasonic irradiation experience a time-averaged drift force that transports them to a minima in the acoustic radiation force potential that is dependent upon the acoustic contrast ratio between the particles and the surrounding fluid. For plane waves, positions that correspond to minima in of the acoustic radiation force potential are the pressure nodal and antinodal planes Other forces are also present in a sound wave that exerts torque on particles, which induces spin or alignment of the particles. Secondary forces between particles, due to scattering of the sound field by neighboring particles, also serves to aggregate particles into concentrated clumps.

Microfluidic devices that incorporate the use of acoustic standing waves may be used to filter particles from samples prior to analysis, or separate and position particles within defined flow channels. Acoustic concentration of biological cells can be incorporated in a fully automated analysis system providing contamination-free high-speed, real-time measurements.

The present invention is an apparatus and method for using acoustic force to position, concentrate, or fractionate particles suspended in a fluid. One embodiment of the present invention uses a low-order coupled structure/cavity mode of a long cylindrical fluid-filled glass tube driven by a piezo-ceramic transducer to create a resonant pressure field that is dipole in character within the fluid-filled cavity. Thus, particles within the fluid are driven towards minima in the radiation force potential created by the resonant ultrasonic field. The cylindrical geometry eliminates the need for accurate alignment of a transducer/reflector system, in contrast to the case where planar, confocal, or traveling wave fields are used. An added benefit of the cylindrical geometry is a lower energy density in the cavity, brought about through excitation of the whole cylinder that results in reduced cavitation, convection, and thermal gradients within the fluid.

U.S. Pat. No. 6,090,295, "Method and Apparatus for Acoustically Demixing Aqueous Solutions", issued on Jul. 18, 2000, by Raghavarao, et al., teaches the use of acoustic energy to demix an aqueous solution that consists of at least two aqueous phases. Here, large amounts of acoustic energy (4-6 Watts/$cm^s$ at 1.2-1.8 MHz) are transmitted from a transducer into an aqueous solution to demix. This differs from the present invention as no resonance modes are utilized to create nodal positions within the aqueous solution and the energy range is such that it would destroy sensitive particles, such as cell structures.

U.S. Pat. No. 5,711,888, "Multilayered Piezoelectric Resonator for The Separation of Suspended Particles", issued on Jan. 27, 1998, by Trampler et al., teaches a method of separating particles suspended within a fluid using acoustic energy. However, the present invention differs in that the cavity is not rectangular, as is taught in Trampler et al., which requires accurate alignment of the system, but instead uses the cylindrically symmetric acoustic modes of the coupled system consisting of the structure and cavity to set up the sought-after resonance and corresponding minima in the acoustic radiation force potential.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes an apparatus and corresponding method for concentrating analytes within a fluid flowing through a tube using acoustic radiation pressure. The apparatus includes a function generator that outputs a radio frequency electrical signal to a transducer that transforms the radio frequency electric signal to an acoustic signal and couples the acoustic signal to the tube. The acoustic signal is converted within the tube to acoustic pressure that concentrates the analytes within the fluid.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1A:
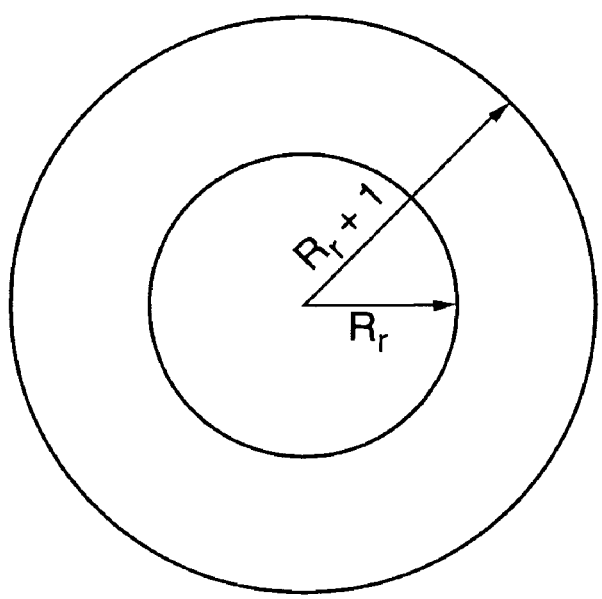
FIGS. 1a and 1b show a cross-section of a cylindrically layered system.

The present invention is an apparatus and method for using acoustic radiation pressure to position, concentrate, or fractionate analytes suspended in a fluid. The natural resonance frequency of a tube is used to concentrate given analytes on the axial center of the tube. A transducer that is attached to the tube provides the acoustic energy. In another embodiment, an additional transducer may also be used for electronic feedback to maintain resonant frequency and for automatic temperature compensation.

Theory

In the first quantitative analysis of the radiation force on a particle in a sound field, King, L. V., "On the acoustic radiation on spheres," *Proc. R. Soc. A.*, 147, 212-240, (1933), considered the acoustic radiation force only. King assumed incompressible spheres, noting that the radiation force on particles with radii less than a wavelength was greater in a standing than a traveling wave field.

L. P. Gorkov, "On the forces acting on a small particle in an acoustical field in and ideal fluid", *Soviet Physics-Doklady*, 6, 773-775 (1962), extended King's analysis to include the influence of particle compressibility on the force moving the particles to nodal or anti-nodal positions.

R. K. Gould, W. T. Coakley, "The effects of acoustic forces on small particles in suspension", in *Proceedings of the 1973 Symposium on Finite Amplitude Wave Effects in Fluids*, edited by L. Bjorno, Pergamon, Guildford, 1974, pp. 252-257, further extended King's analysis to include buoyancy, and acoustic streaming.

Lastly, K. Higashitani, M. Fukushima, Y, Matsuno, "Migration of suspended particles in plane stationary ultrasonic field", *Chem. Eng. Sci.* 36, 1187-1192 (1981), developed terms to account for diffusion of small particles. Following the findings of these authors a quantitative understanding of particle movement in an ultrasonic field was obtained.

For a dilute suspension in an arbitrary field, Gorkov's theory for non-interacting particles provides a good description of the equilibrium particle distribution. The time-averaged potential acting on a small spherical particle of radius r and density $\rho_p$ in a fluid of density $\rho_f$ in an acoustic field is defined as:

$$U = 2\pi r^3 \left[ \frac{\overrightarrow{p_{in}^2}}{3\rho_f c_f^2} \frac{c_p^2 \rho_p - c_f^2 \rho_f}{c_p^2 \rho_p} - \rho_f \overrightarrow{v_{in}^2} \frac{(\rho_p - \rho_f)}{2\rho_p + \rho_f} \right] \quad (1)$$

where $c_f$ and $c_p$ are the acoustic velocities in the fluid and the given particle respectively, $p_{in}$ and $v_{in}$ are the mean-square fluctuations of the pressure and velocity in the wave at the point where the particle is located. In the case of a plane wave, depending on the relationships between the density and acoustic velocity of the given particle and fluid, the given particle will tend to move either to a pressure anti-node or a pressure node. The velocity and pressure of the acoustic field can be derived utilizing methods such as the global matrix method described below.

Referring now to FIG. 1a, a cylindrically layered system can be modeled using the direct global matrix approach taught by D. C. Ricks, H. Schmidt, "A numerically stable global matrix method for cylindrically layered shells excited by ring forces," *J. Acoust. Soc. Am.* 95, 3339-3349 (1994). The layers of material are numbered n=1 to N where layer 1 includes r=0 and layer N extends to infinity. The variable $r_n$ corresponds to the boundary between layer n and n+1. All layers are assumed to be isotropic and homogeneous viscoelastic with Lame constants $\lambda_n$ and $\mu_n$ and density $\rho_n$. The subscript refers to the layer number described by the constants. If the layer is a solid then the displacement field $U_n$ is governed by the following 3-D equations of elastodynamics:

$$(\lambda_n + 2\mu_n)\nabla\nabla \cdot \overrightarrow{U}_n - \mu_n \nabla \times \nabla \times \overrightarrow{U}_n + f_n = \rho_n \overrightarrow{\ddot{U}}_n \quad (2)$$

The variable $f_n$ refers to the applied force per unit volume in layer n. The longitudinal and shear wave speeds in layer n are related to the Lame coefficients as described by:

$$C_{ln} = \sqrt{(\lambda_n + 2\mu_n)/\rho_n}, \quad (3)$$

$$C_{sn} = \sqrt{\mu_n/\rho_n} \quad (4)$$

The corresponding wave numbers $h_n$ and $k_n$, the longitudinal and shear wave numbers, respectively, are expressed in terms of the angular frequency $\omega$ and the sound speeds. Here $C_{ln}$ is the longitudinal wave speed in a given elastic material, and $C_{sn}$ is the shear wave speed in a given elastic material:

$$h_n = \omega/C_{ln}, \quad (5)$$

$$k_n = \omega/C_{sn} \quad (6)$$

In fluids, any terms involving $c_{sn}$ and $k_n$ are ignored, as there are no shear forces within a fluid, and $\mu_n=0$. A time dependent ring force of $e^{-i\omega t}$ can be assumed without loss of generality as a time harmonic field of frequency ($\omega$) can be written as an infinite sum of harmonic functions (Fourier Series). Therefore, the time dependence of other forcing functions, including a point or line excitation, can be synthesized from time-harmonic forces by using a Fourier integral over frequency. Similarly angular dependence of $e^{iv\theta}$ is assumed, where v is the order. The displacement field can be expressed as the linear superposition of homogeneous and particular solutions. The homogeneous solutions are source-free waves that would emanate from the ring forces in layer n if the layer extended over all space which, when added to the particular solutions, satisfy the boundary conditions. Therefore, the homogeneous field is governed by:

$$(\lambda_n+2\cdot\mu_n)\nabla\nabla\cdot\vec{U}_n^H-\mu_n\nabla\times\nabla\times\vec{U}_n^H+\rho_n\omega^2\vec{U}_n^H=0 \qquad (8)$$

The field can be expressed in terms of scalar displacement potentials that satisfy the Helmholtz equations. The problem may be further reduced to radial and azimuthal coordinates Although any two of the Bessel and Hankel functions would satisfy the resulting differential equations, numerical stability dictates that the solutions be represented in terms of the Bessel and Hankel function of the first form $H^{(1)}_v$. The coefficients are determined using the boundary conditions for each layer. The global matrix is constructed using the unknown displacements and stresses associated with the homogeneous waves, written in terms of an amplitude vector and set equal to the displacements and stresses due to the particular solutions due to the forcing excitation. Solutions for the coefficients are determined by applying Cramer's rule to the global matrix.

Figure 1B:
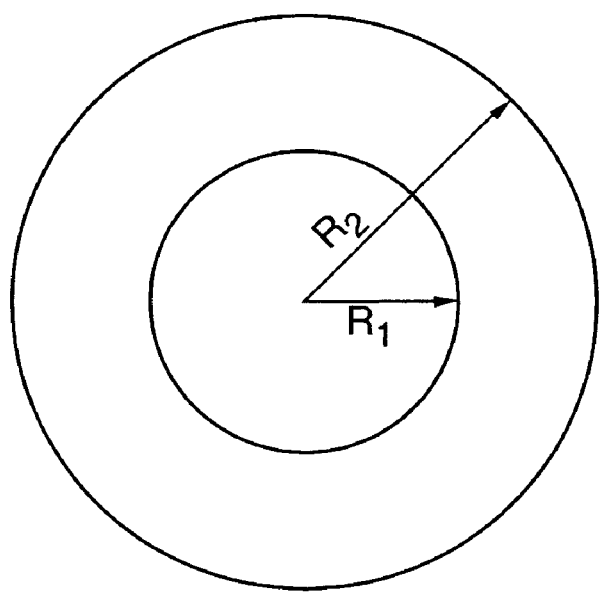

Referring now to FIG. 1b, the boundary conditions, which generate the global matrix, are:

$$\vec{U}_{r1}^H(R1)=\vec{U}_{r2}^H(R1), \qquad (9)$$

$$\vec{\tau}_{rr1}^H(R1)=\vec{\tau}_{rr2}^H(R1), \qquad (10)$$

$$\vec{\tau}_{r\theta2}^H(R1)=0, \qquad (11)$$

$$\vec{\tau}_{rr2}^H(R2)=\vec{\tau}_{rr}^P(R2), \text{ and} \qquad (12)$$

$$\vec{\tau}_{r\theta2}^H(R2)=\vec{\tau}_{r\theta}^P(R2). \qquad (13)$$

The variables R1 and R2 are the internal and external tube radii respectively. The boundary conditions require coritinuity of displacement at the inner boundary R1. The radial stress is continuous at R1. Since the cylinder is fluid filled, no shear stress is present at the fluid-solid interface at R1. Since the system is being driven at the outer surface, radial and angular stresses are continuous and equal to the particular solutions at the outer boundary R2.

The finite width of the element was accounted for in the calculations by applying a Gaussian weighting function about the point $\theta=3\pi/2$ radians to the forcing function of the particular solutions.

Thus, the boundary value problem presented above is numerically solved to describe the motion of a line driven tube. The results are used to predict the vibrational behavior of outer boundary of the tube and the cavity within the tube. This in turn is used to describe the ability of the tube to concentrate particles and predict the necessary motions for efficient concentration

EXAMPLE 1

Figure 2:
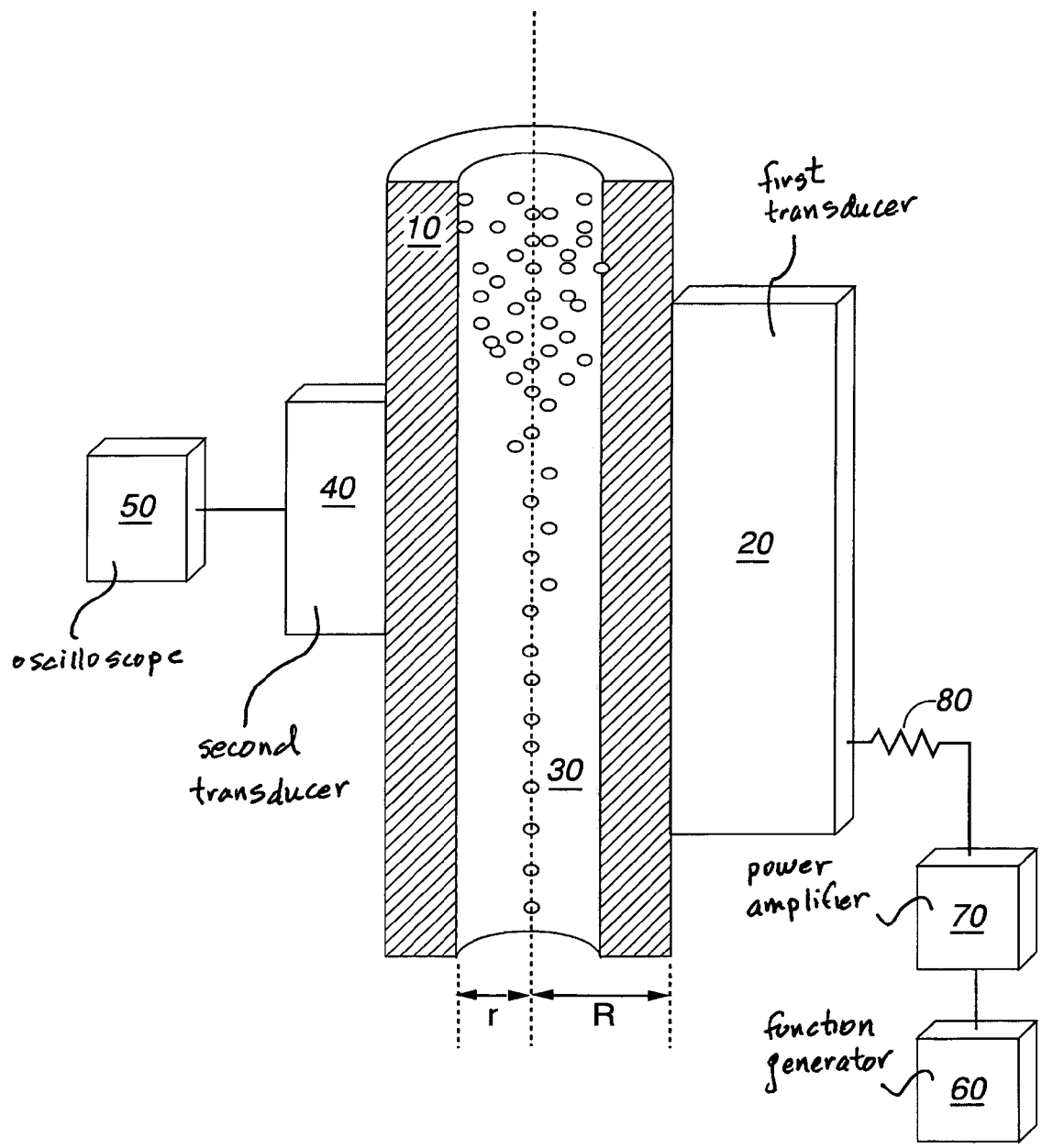
FIG. 2 pictorially illustrates an experimental setup using a glass tube for practicing the present invention.

Referring now to FIG. 2, first transducer 20 was connectively attached, axially to cylindrical glass tube 10 with inner diameter r of 2.2 mm, and outer diameter R of 3.97 mm. In preferred embodiments, materials used for tube 10 include glasses, plastics, metals, or crystalline solids. Since the entire length of the tube structure is excited, a tube of greater length increases residence times of the particles in the acoustic field in the fluid generated by the elongated structure.

In one embodiment, the dimensions of first transducer 20 were 30 mm long, 3 mm thick, and 1.5 mm wide, with a corresponding thickness mode resonance of 420 kHz determined by measurement with an impedance analyzer. First transducer 20 used in this example was lead zirconate titanate, but may be selected from any transducer known to those practiced in the art, to include: piezoceramic, piezosalt, piezopolymer, piezocrystal, magnetostrictive, or electromagnetic transducers. The resonance of the system, defined as the frequency of forced oscillation, (marked by an increase in the oscillatory energy absorbed by and transferred into the system) was determined to be approximately 417 kHz by scanning the drive frequency of function generator 60 to find the point of particle concentration observed within glass tube 10.

Second transducer 40, also connectively attached to glass tube 10, was used for tuning the drive frequency to the resonance of the structural acoustic mode of the system. Note that in another embodiment, second transducer 40 may be used to provide electronic feedback to maintain resonant frequency and automatic ambient temperature compensation of the system. The tuning signal was viewed on oscilloscope 50. Tuning was achieved by varying the drive frequency to maximize the received tuning signal as observed on oscilloscope 50. Second transducer 40 may also be selected from piezoceramic, piezosalt, piezopolymer, piezocrystal, magnetostrictive, or electromagnetic transducers.

First transducer 20 was driven using 30V function generator 60 that provided a radio frequency electrical signal, which was then passed through 75 W power amplifier 70 to amplify the signal. Note that power amplifier 70 is not needed to practice the present invention, but is included in a preferred embodiment. Any voltage source circuit known to those skilled in the art that is capable of producing a variety of voltage waveforms of varying frequencies may be used for function generator 60. Typical drive signal amplitudes into first transducer 20 were 10-12 Vpp and 80 mA. The signal current was measured as a voltage across 10-ohm resistor 80 in series with first transducer 20.

Ten-micron particles, with a standard deviation of 0.7 microns, were diluted to a concentration of approximately 0.025% by volume in distilled water, and then flowed through glass tube 10 at a flow rate of 5-25 mm/s using a gravity feed water system. The liquid was not degassed in order to most accurately mimic the conditions expected in a microfluidic system, and was only minimally stirred in order to maintain suspension of the particles in solution while within the feed water reservoir.

The outer boundary surface displacement of glass tube 10 was calculated using the theoretical model described above. Particle concentration to the central axis of the tube occurs when the coupled structure/cavity mode becomes dipole in character as defined by the external surface displacements of the tube. Calculations determined this mode to occur at frequency 417 kHz for the configuration described. The material properties of the glass were determined by matching index of refraction, density, longitudinal sound speed, and coefficient of thermal expansion to soda lime glass. A longitudinal sound speed of 5900 m/s, shear sound speed of 3300 m/s, and density of 2.43 g/cm$^3$ were used for the glass. The values of sound speed and density of air used in the calculations were 340 m/s and 10$^{-6}$ g/cm$^3$ respectively. Water was assumed to have sound speed of 1487 m/s and density of 1 g/cm$^3$. Pre-experimental modeling of the system allows for accurate identification of particular structural modes with maximal acoustic concentration efficiency.

Figure 3:
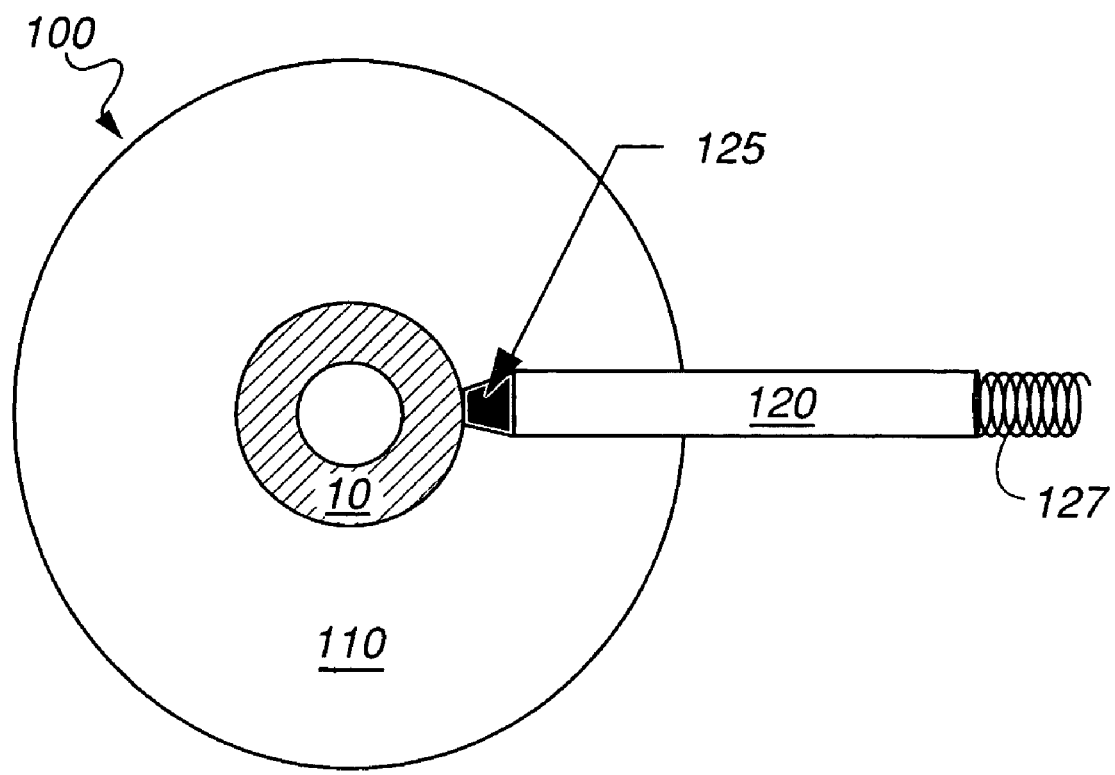
FIG. 3 pictorially illustrates an angle scan apparatus used to measure surface vibration of a glass tube used to practice the present invention.

Referring to FIG. 3, angle scanning apparatus 100 was used to determine the surface vibration of glass tube 10, allowing verification of the desired mode of excitation on the outer boundary of glass tube 10. Glass tube 10 was mounted to computer controlled angular stepper motor stage 110 and probed with a narrow transducer (pinducer) 120. Half hemisphere of solder 125 was affixed to pinducer 120 to assure point contact with glass tube 10, thus minimizing the angular integration of the signal. To maintain constant contact with glass tube 10, pinducer 120 was mounted on spring 127.

Figure 4:
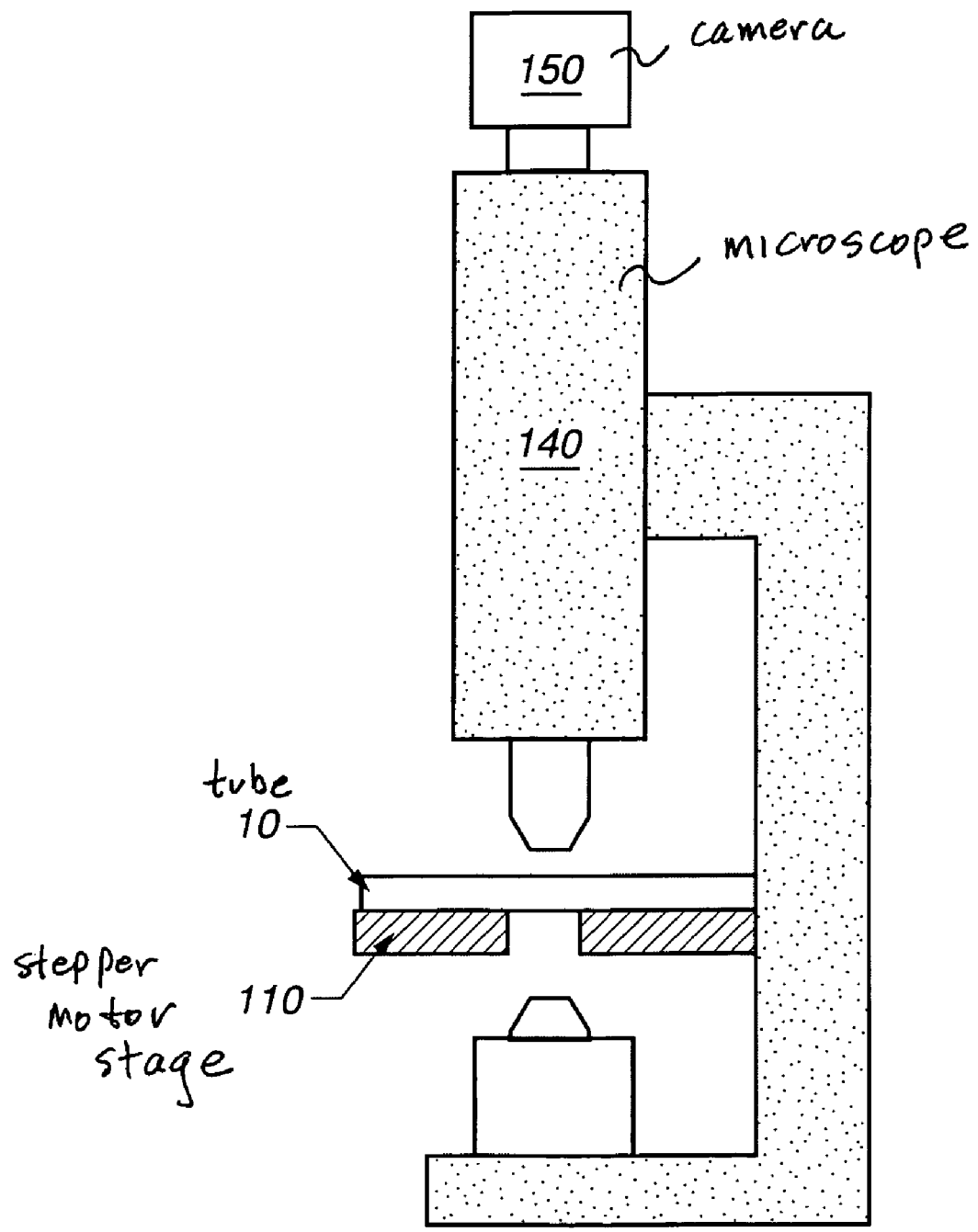
FIG. 4 pictorially illustrates a bottom-illuminated microscope used to image the particle concentration pattern within water flowing through a glass tube used to practice the present invention.

Referring to FIG. 4, computer controlled 12-bit digital oscilloscope 50 was used for data collection. Tube 10 was measured using the above apparatus for both air-filled and water-filled cases. Images of the resulting concentration pattern were taken using bottom-illuminated microscope 140 and 1280×1024 12-bit digital camera 150.

Theory predicted and experimental measurements were taken first with glass tube 10 filled with air and then with glass tube 10 filled with flowing water, in order to compare the outer boundary states of both configurations.

Figure 5:
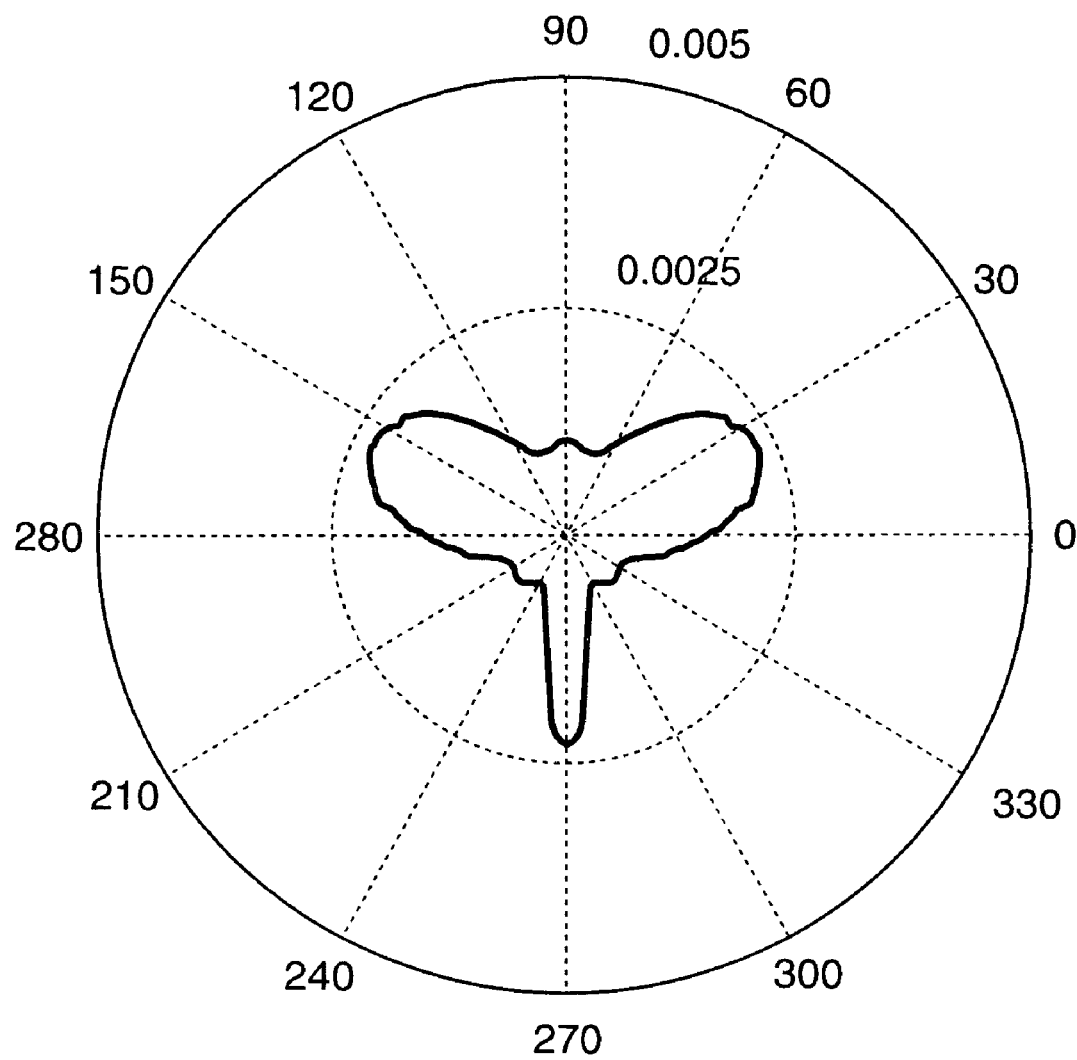
FIG. 5 graphically shows predicted outer boundary surface displacement of an air filled glass tube.
Figure 6:
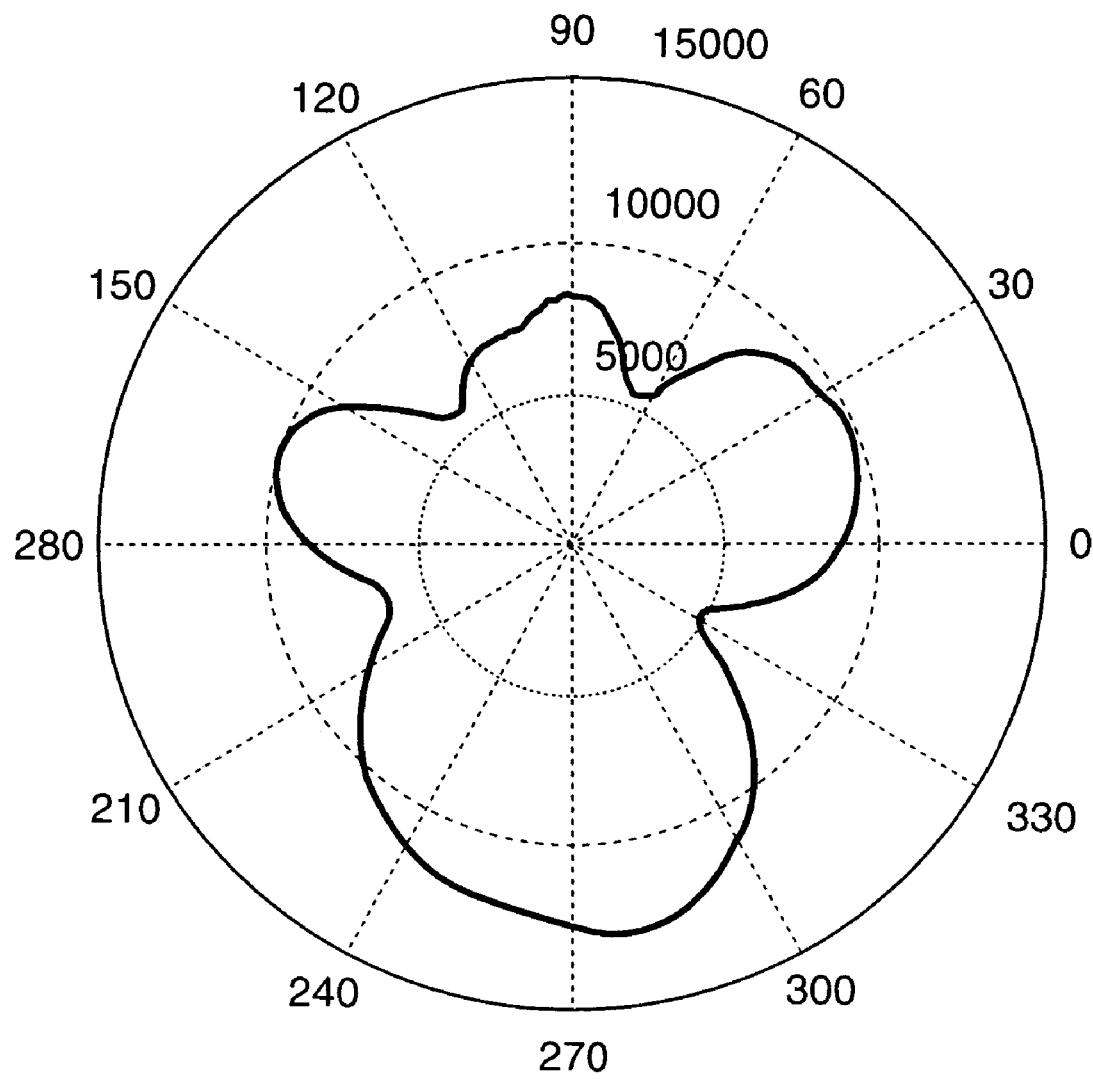
FIG. 6 graphically shows experimentally measured outer boundary surface displacement of an air filled glass tube.

FIG. 5 shows the theory predicted surface displacement of the outer boundary of an air filled glass tube 10. The corresponding measured surface displacement found in the experiment is shown in FIG. 6. The demarcations around the polar axis are given in degrees, while the radial axis indicates the absolute value of displacement in both figures. Three primary lobes at approximately 120-degree relative angles and a directly opposite smaller lobe are seen in both the calculated and measured result. The greater angular spread in the measured data was due to width of angular coupling of the drive transducer 20.

Figure 7:
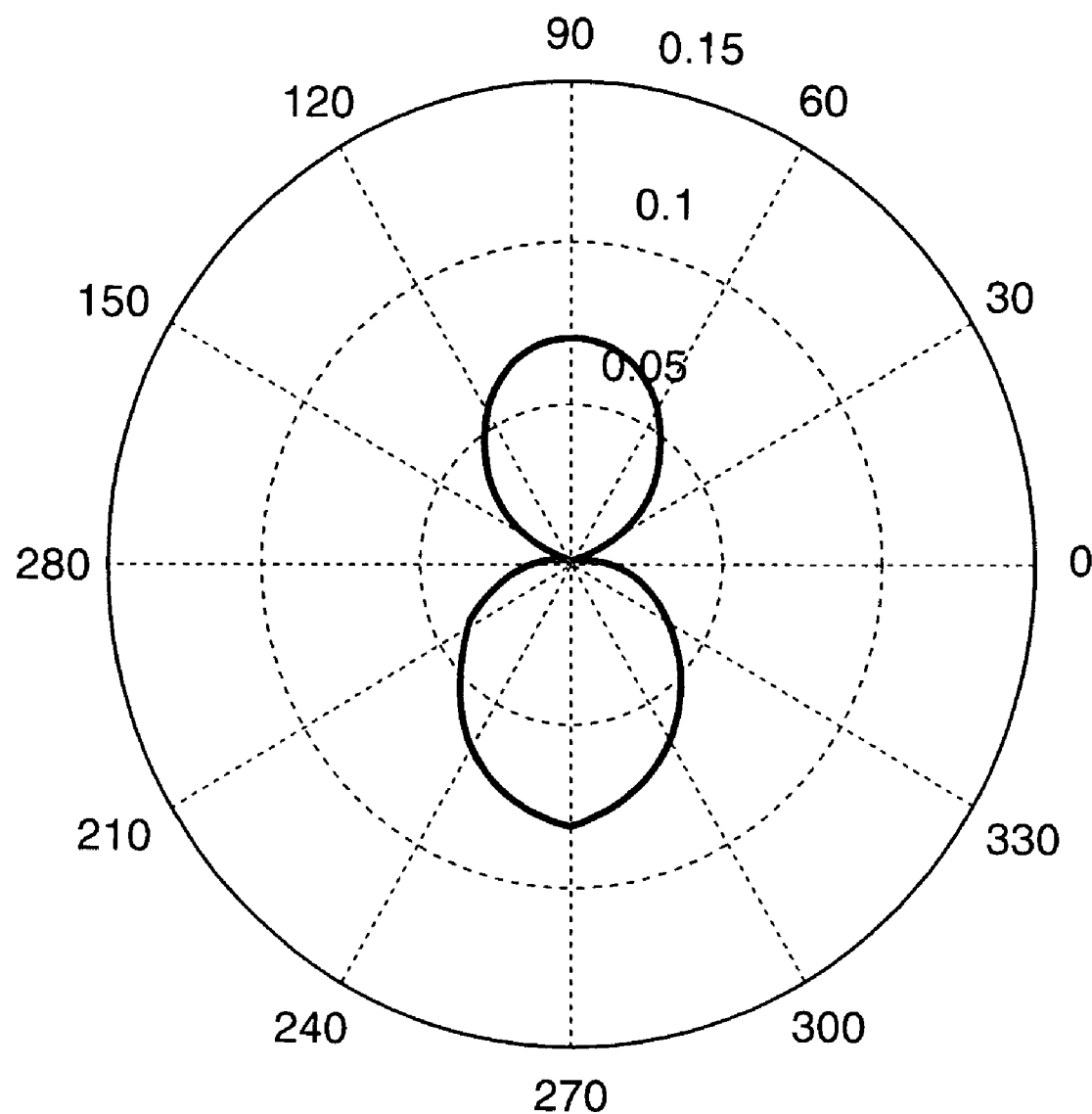
FIG. 7 graphically shows predicted outer boundary surface displacement for a water filled glass tube.
Figure 8:
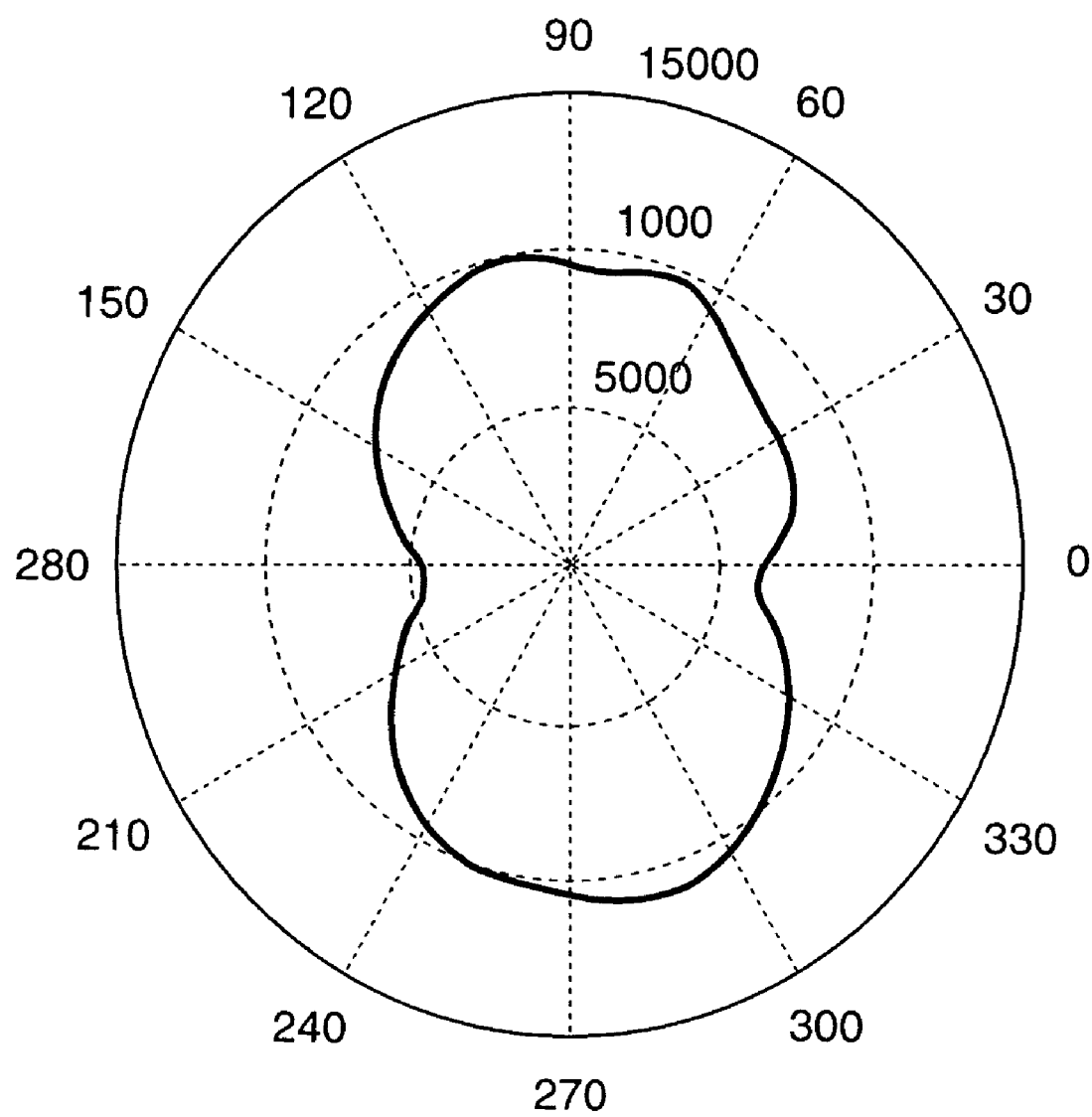
FIG. 8 graphically shows experimentally measured outer boundary surface displacement for a water filled glass tube.

When glass tube 10 was filled with flowing water, the four lobed external displacement shown in FIG. 6 collapsed to a strong dipole, as can be seen in both the theory predicted result shown in FIG. 7, and the experimental outer boundary displacement shown in FIG. 8. Thus, it was concluded that the preferred mode of vibration for a cylindrical tube is a dipole.

Figure 9:
FIG. 9 is a micrograph of 10-micron particles within water flowing though a glass tube prior to practicing the present invention.
Figure 10:
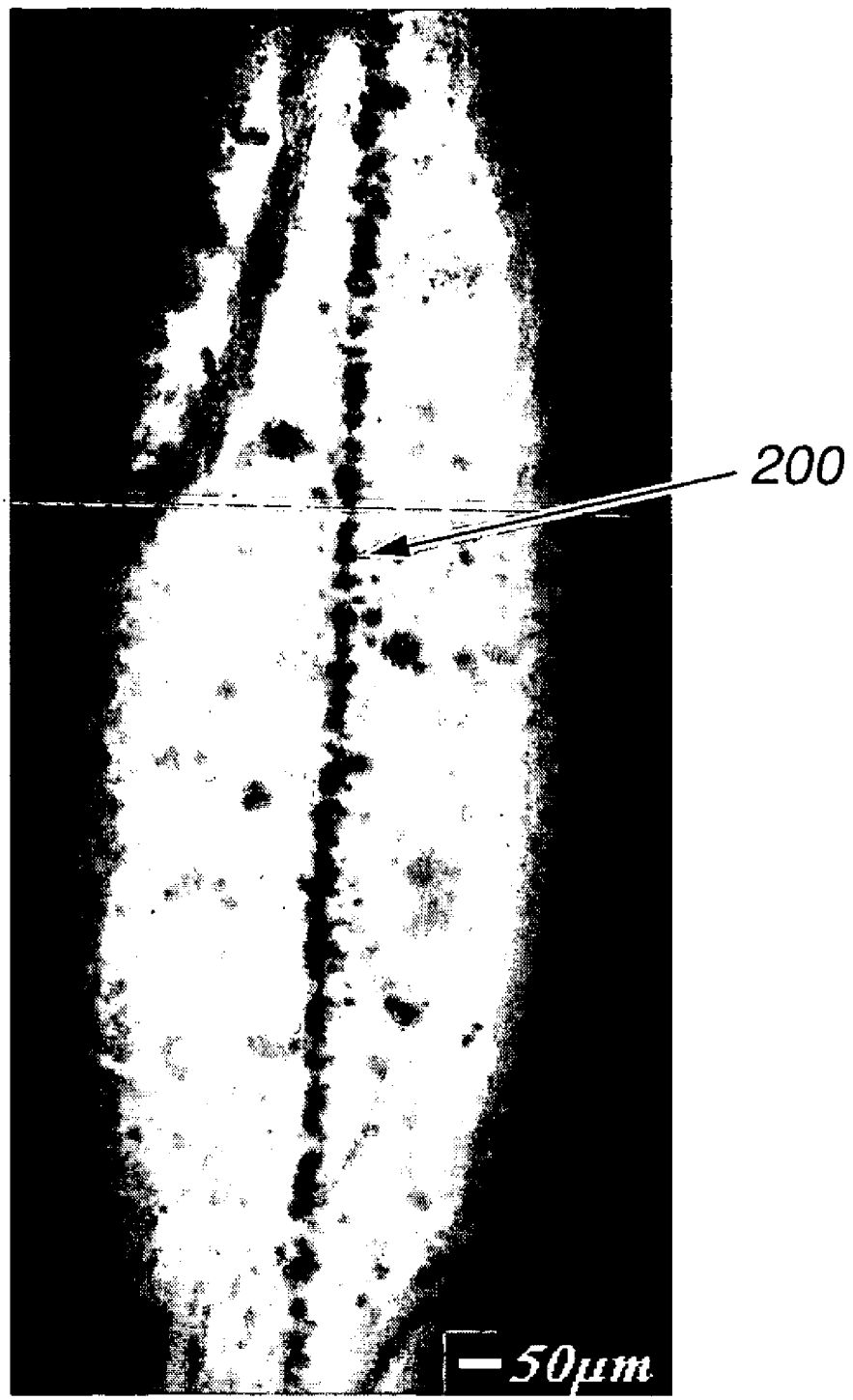
FIG. 10 is a micrograph showing the concentration of 10-micron particles within a fluid passing though a glass tube while practicing the present invention.

Particles (latex microspheres) were then added to the flowing water. FIG. 9 shows the particle concentration pattern prior to energizing first transducer 20. Tube 10 was then subjected to 0.8-0.9 W with drive transducer 60. Referring to FIG. 6, it took approximately 5 seconds to form particle concentration line 200 that is only a few particle diameters across.

Various concentrations of particles ranging from 0.02% to 0.2% by weight were investigated. No significant differences were observed in concentration times, but experiments involving concentrations of particles greater than 0.1% by weight showed increased agglomeration due to the secondary forces discussed earlier. Note, the agglomerations were also concentrated at the center, but did not disassociate at power levels less than 1 W.

Particle concentration was observed using low input power, without the necessity of careful transducer/system alignment inherent in devices described in prior art. Traditionally, when opposing transducers are used in a cavity, the position of the transducer is used to adjust the resonance of the cavity. Over time, the transducers misalign from small jolts to the system. Additionally, the traditional methods of acoustic concentration utilize quarter wave matching layers, half-wavelength cavities and require careful alignment for an axially non-symmetric system. Using an inherently symmetric geometry for the system eliminates the need for careful alignment.

In traditional acoustic separation and manipulation techniques, the acoustic field is only present directly in line with the exciting transducer. In flowing systems, the residence time of the particles in the acoustic field is limited by the physical size of the transducer. This limitation demands that larger amounts of energy be pumped into the transducer to compensate for this short interaction time scale. This large energy pumping into the flow volume leads to large temperature fluctuations, cavitation, and convection.

However, in the present invention, by exciting the entire tube structure, the active region is not limited by the size of the transducer, but rather by the size of the structure. The acoustic field is dispersed throughout this larger volume leading to significantly lower acoustic energy densities within the flow stream. Thus, temperature effects are not induced and residence times of the particle in the field are dramatically increased.

Correspondence of concentration to a dipole mode of the system was shown. Reduction of the elastodynamic equation to two dimensions has proved to be a reasonable simplification. The validity of the global matrix model for the vibration has also been demonstrated. Application of this model to determining optimal material properties and geometric parameters for particle concentration has been proved.

EXAMPLE 2

Figure 11:
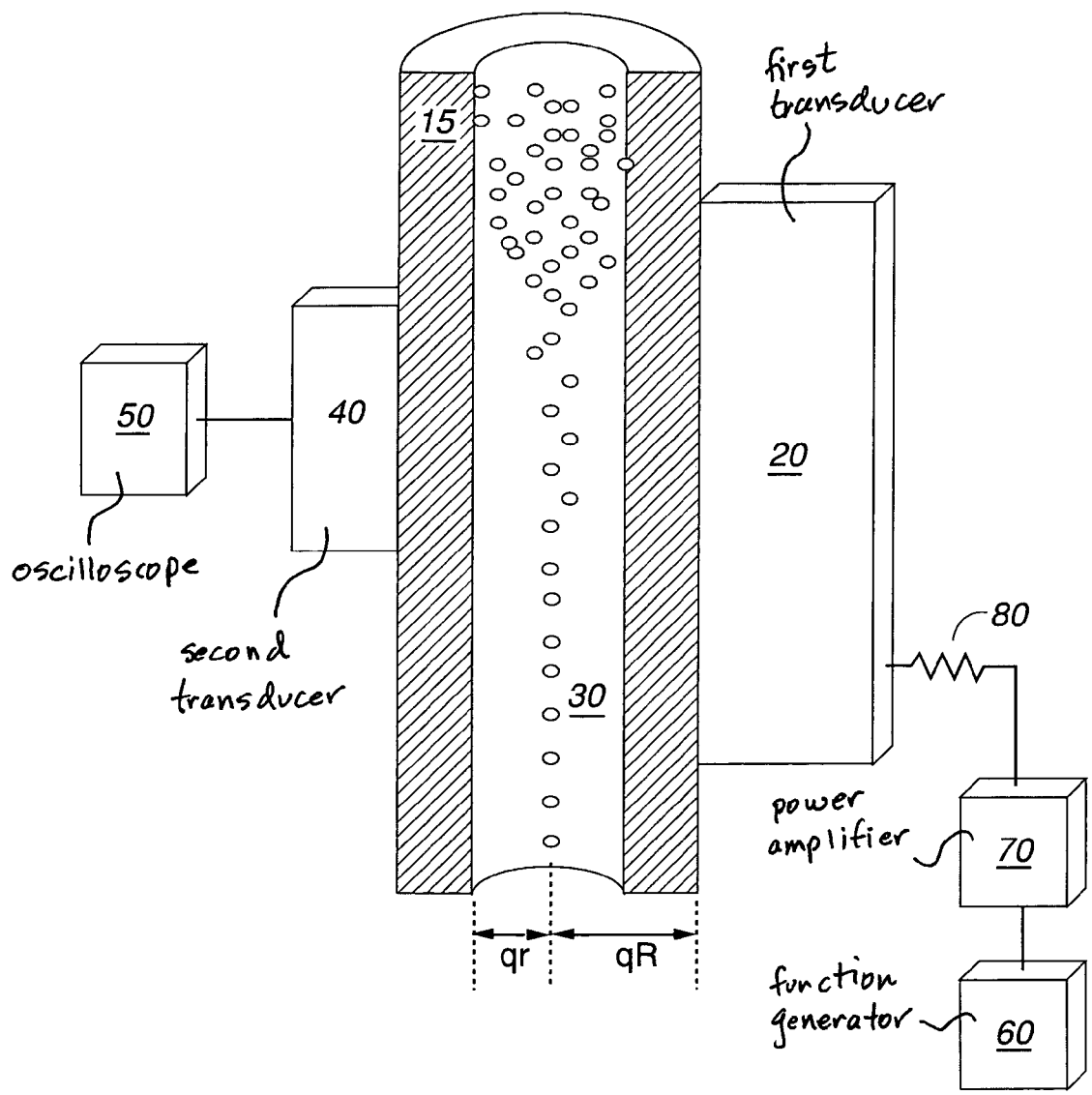
FIG. 11 pictorially illustrates an experimental setup using a quartz tube for practicing the present invention.

Referring now to FIG. 11, thick-walled, cylindrical quartz tube 15 was tested for comparison with the glass tube in Example 1. Quartz tube 15 had inner diameter qr of 2.0 mm and outer diameter qR of 7.85 mm. First transducer 20 was again, connectively attached, axially to quartz tube 15 as in Example 1.

Figure 12:
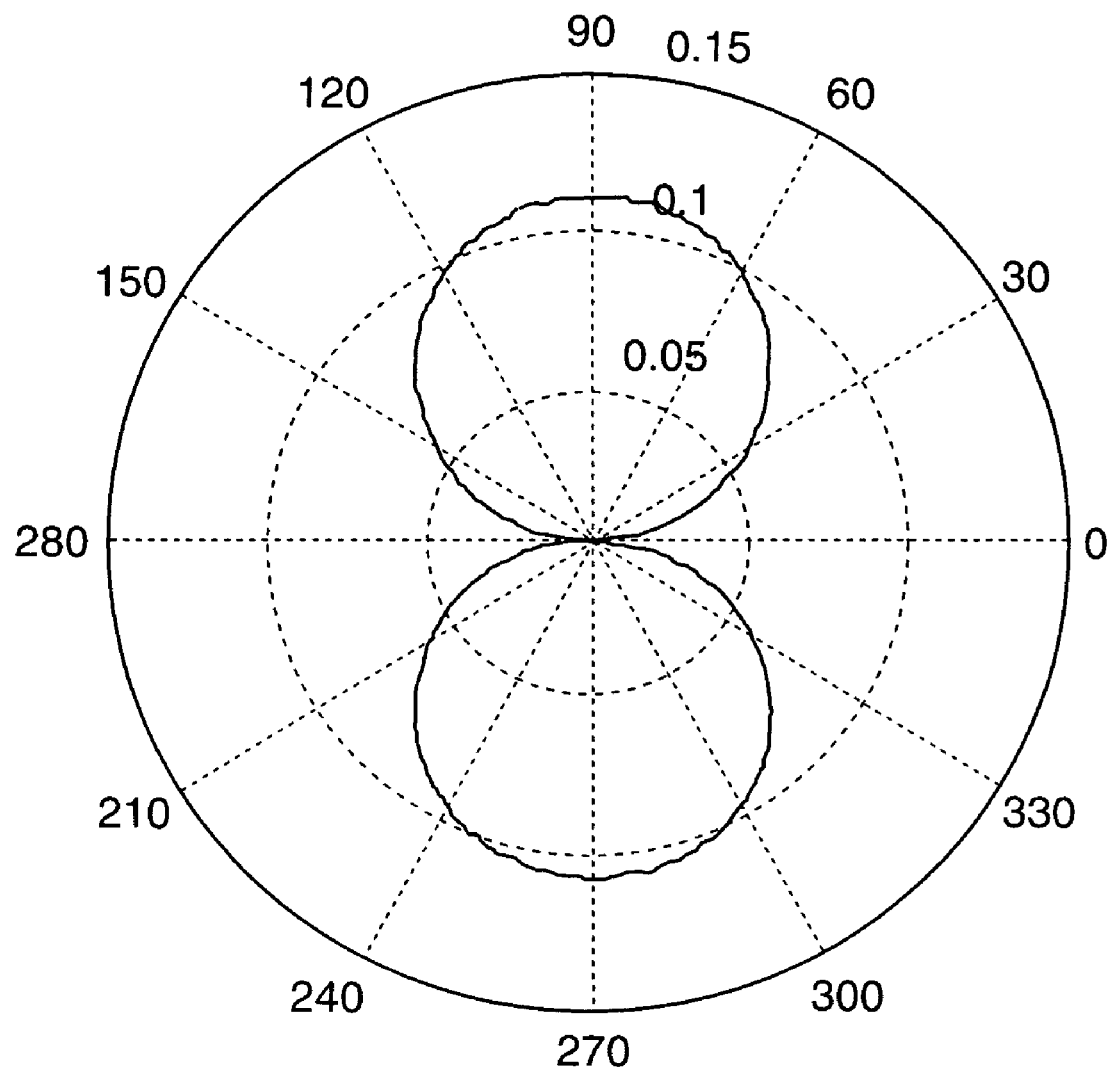
FIG. 12 graphically shows predicted outer boundary surface displacement for a water filled quartz tube.
Figure 13:
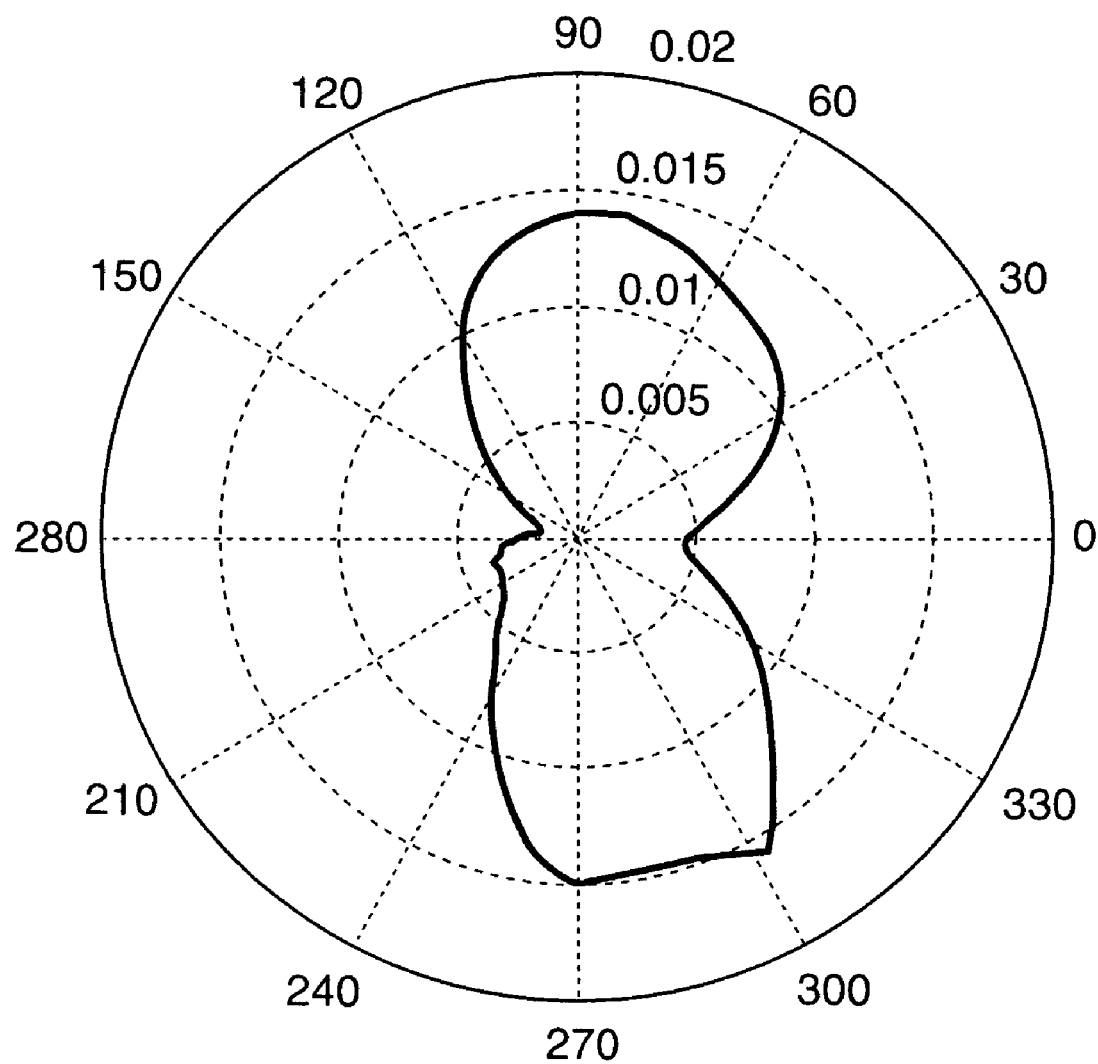
FIG. 13 graphically shows experimentally measured outer boundary surface displacement for a water filled quartz tube.

The material properties of quartz tube 15 were: longitudinal sound speed of 5700 m/s, transverse sound speed of 2650 m/s and density of 2.65 g/cm$^3$. The same properties of air and water as used in Example 1 were used for Example 2. The theoretical model outer boundary surface vibration predicted a dipole at 462 kHz for quartz tube 15, shown in FIG. 12. Actual surface vibration measurement yielded the results shown in FIG. 13. As can be seen, there was good correspondence between the predicted and experimental results. It is worth noting that the predicted strength of dipole vibration in quartz, as shown in FIG. 12, was greater than that of glass, as shown in FIG. 9. Thus, it is to be expected that, for equal power input, quartz tubing will demonstrate a tighter focusing of the particles within the flowing water.

Figure 14:
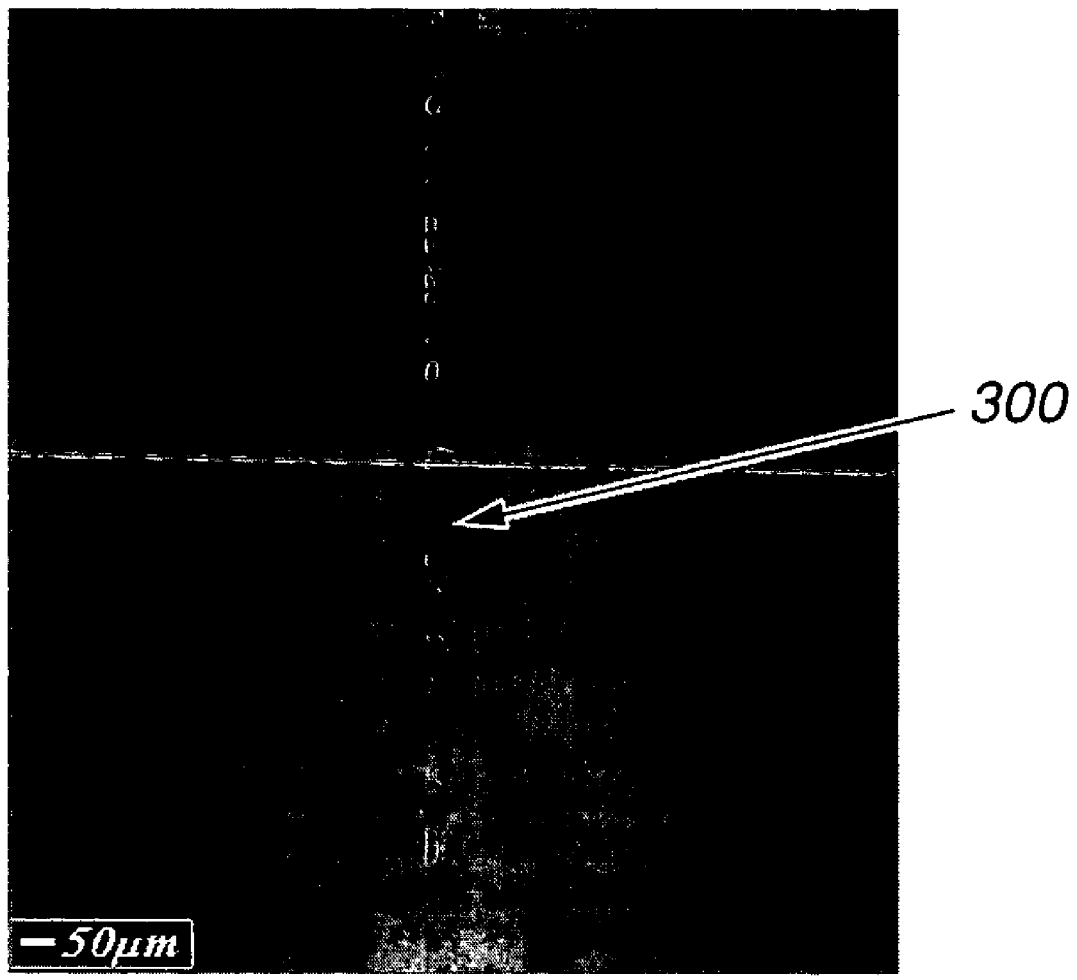
FIG. 14 is a micrograph of 10-micron particles concentrated within water flowing through a quartz tube at 462 kHz.

In order to verify this assertion between dipole vibration and concentration, particles were fed through the quartz tubing and the concentration pattern at 462 kHz was imaged. A micrograph of the resulting particle concentration pattern is shown in FIG. 14. Note the dipole does correspond to a frequency at which concentration takes place, and, furthermore, concentrated particles 300 form a more focused line using quartz versus glass.

APPLICATION

The most common premise for low power acoustic concentration is the requirement of quarter wave matching layers. In this type of system, the incident acoustic disturbance is resonantly amplified in the matching layers yielding higher energy transmission efficiencies. However, the inherent alignment problems of either planar or confocal geometries, even in the traveling wave case, for proper positioning, make the process more difficult.

The creation of strongly exciting cavity modes, created by driving at far below quarter wave thickness of a cylinder wall, offers some intriguing possibilities for applications. For example, the ability to discriminate, analyze, and quantify distinct populations of biological cells/cell organelles has become increasingly important with the growing trend to focus biological studies on various cell types. Flow based cytometry and cell sorting are unique techniques that permit the identification, analysis, and purification of cells based on their expression of specific chemical markers. Furthermore, flow cytometry analysis of biochemical reactions on both cells and arrays of microspheres is a burgeoning field that is becoming widely used in biomedical, biochemical and genomic assays.

Figure 15:
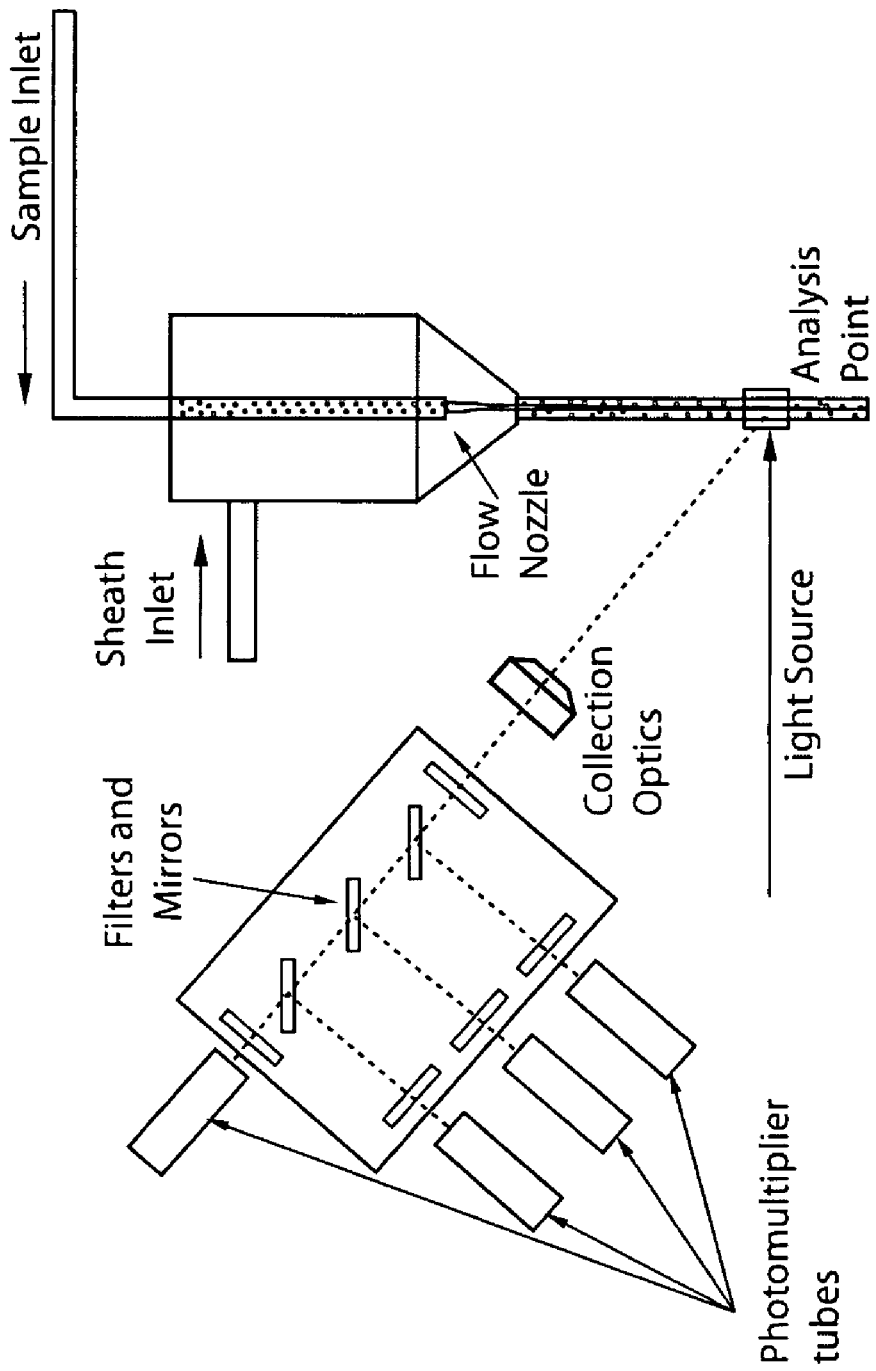
FIG. 15 pictorially illustrates a prior art conventional flow cytometer setup.

The very fine positioning provided by hydrodynamic focusing of the present invention is a critical application to precise measurements using a flow cytometer. Referring to FIG. 15, a conventional flow cytometer uses hydrodynamic focusing to generate a narrowly focused, concentrated sample stream of analytes (5-10 µm in diameter) moving at a high linear velocity (1-10 m/s), which is subjected to tightly focused (10-100 µm diameter) laser beams (or other tightly focused light source such as an arc lamp). Within the interrogation volume, formed by the intersection of the laser and the sample stream, light scatter along with several wavelength bands of fluorescence from the interaction with analytes are collected using high Numerical Aperture optics (e.g. microscope objectives or aspheric lenses) and sensitive optical detectors such as photomultiplier tubes (PMTs), avalanche photodiodes (APDs), photodiodes, and array based detectors such as CCD or CMOS array systems. The collected wavelength bands are then compared to a library of wavelength bands associated with known elements and molecules to identify the chemical composition of the analytes.

Analytes under analysis, like cells and microspheres (~10 µm in diameter), largely exclude free fluorophores from the interrogation volume. Therefore, background from unbound fluorescent probes is low, which allows sensitive measurement of particle-associated probes without separation steps. Flow cytometers can detect as little as a few hundred fluorophores at conventional flow rates (m/s), and single fluorophores with reduced flow rates (cm/s). The high linear velocity and small interrogation volume of conventional cytometers results in transit times of a few µs, requiring the use of high speed analog-to-digital converters (ADCs), operating at rates as fast as 20 MHz, to record the fluorescence and scatter signals. Note that for practitioners of the art, additional modalities, such as collection of Raman light scatter and magnetic moment detection with flow cytometers equipped with a superconducting quantum interference device (SQUID) or giant magnetoresistive (GMR) detector, may also be utilized.

Figure 16:
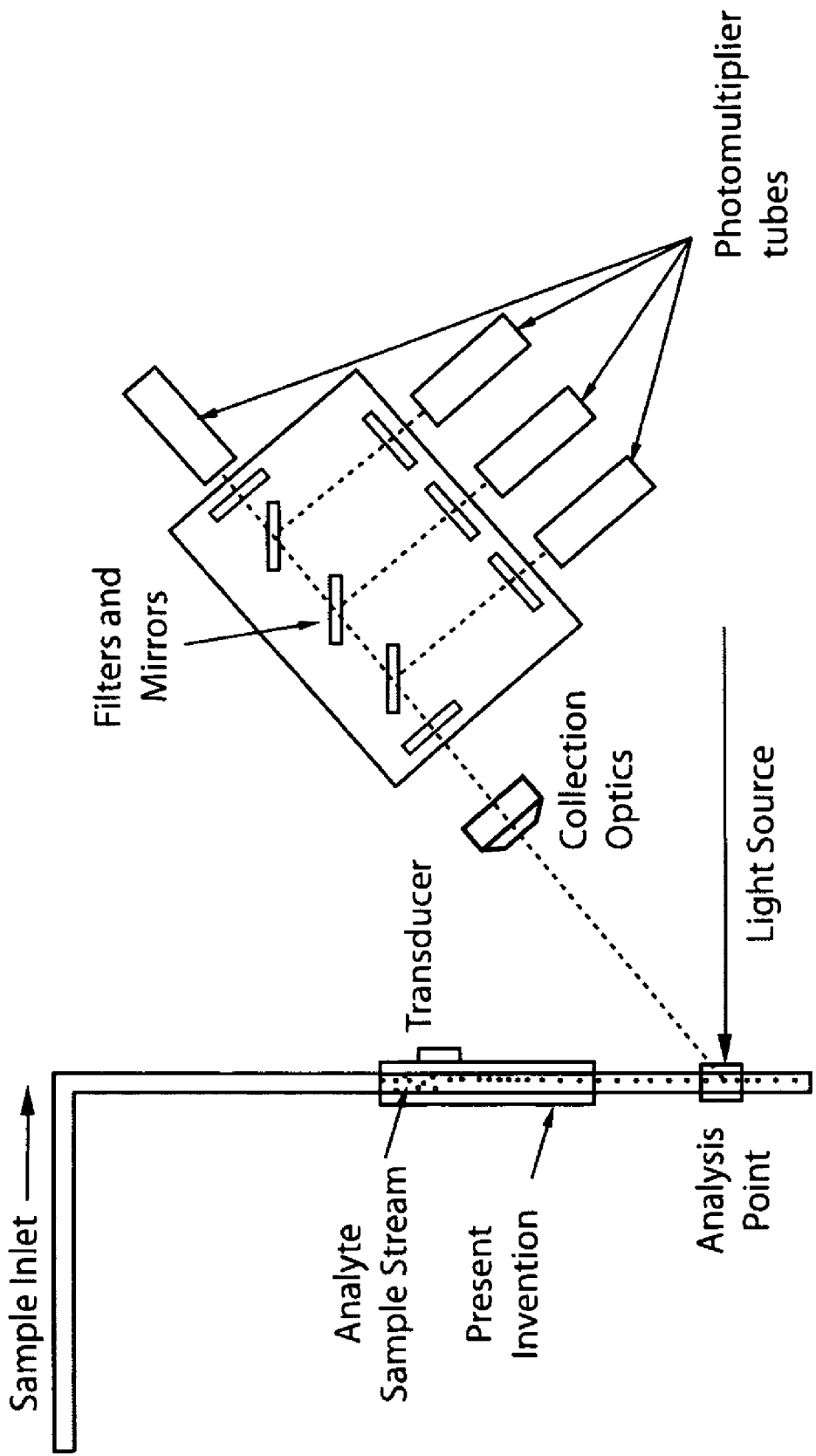
FIG. 16 pictorially illustrates a flow cytometer setup using the present invention.

The present invention may be used to acoustically focus analytes for analysis rather than using conventional hydrodynamic focusing. Acoustic focusing eliminates the need for a hydrodynamic sheath, as well as allowing for high analysis rates at lower linear velocities. Referring now to FIG. 16, in an acoustic focusing flow cytometer, the present invention is used in place of the hydrodynamic focusing nozzle of conventional cytometers to achieve a tightly focused, concentrated sample stream of analytes. Thus, the sample stream is interrogated in an identical fashion to conventional flow cytometers, but does not require sheath flow and associated equipment to focus the sample stream, allowing for increased instrument portability and reduced consumable costs.

Figure 17A:
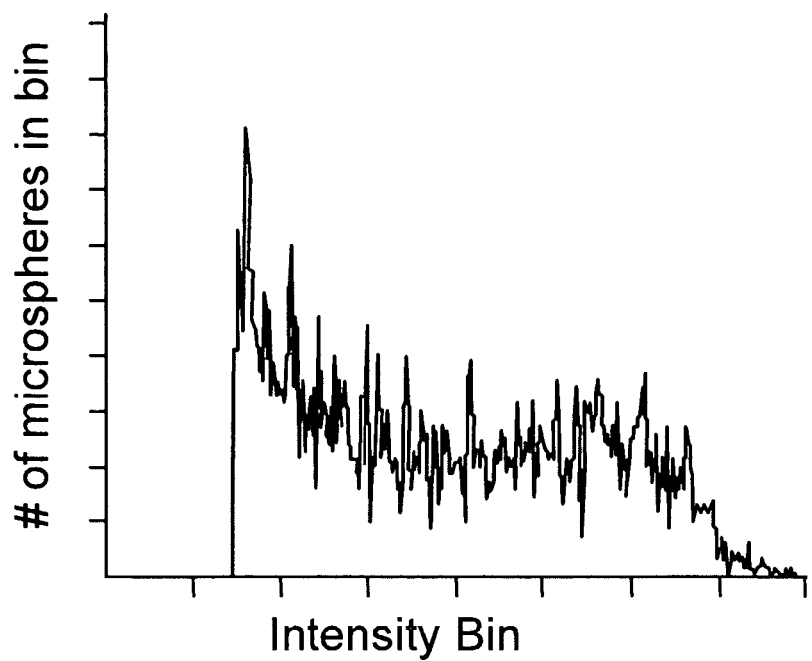
FIGS. 17a and 17b graphically show one dimensional histograms of the fluorescence collected from uniformly stained fluorescent microspheres in unfocused (17a) and acoustically focused (17b) fluid streams.
Figure 17B:
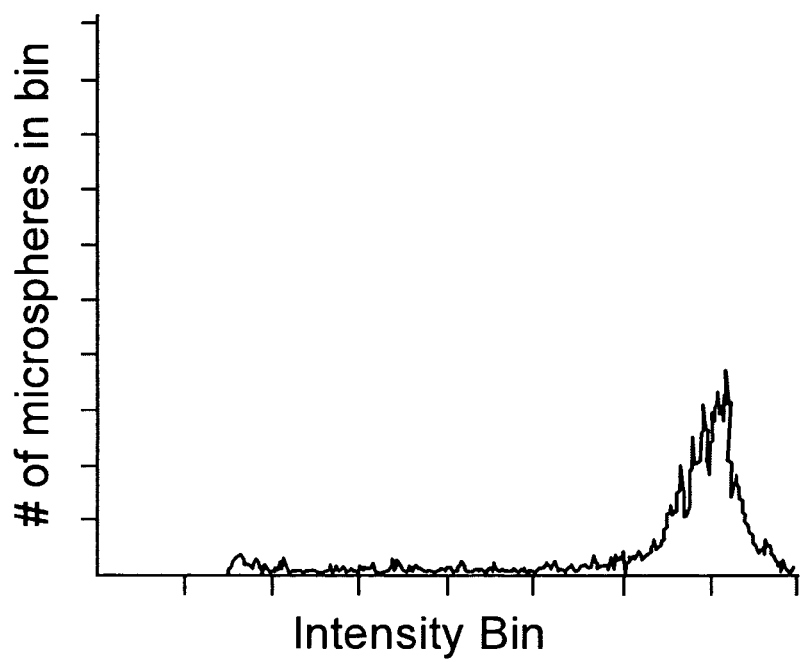

Results demonstrating acoustic focusing in a flow cytometer without sheath flow, as shown in FIG. 16, are shown in FIGS. 17a and 17b. FIG. 17a graphically shows a one-dimensional histogram of measured fluorescence collected from uniformly stained fluorescent microspheres in an unfocused fluid stream. FIG. 17b graphically shows a one-dimensional histogram of measure fluorescence collected from uniformly stained fluorescent microspheres in an acoustically focused fluid stream practicing the present invention. The x-axis corresponds to measured fluorescence intensity bins and the y-axis corresponds to the number of particles in each of the bins. A laser was used to illuminate the uniformly stained fluorescent particles (10 micron diameter) in a cylindrical cavity.

FIG. 17a shows that, because the microspheres are not focused into a particular region of the flowing stream, they are excited by varying intensities of the focused laser beam as it traverses flowing stream. The inconsistent illumination is due to random positioning as exhibited by the high degree of variation in the emitted fluorescence. The wide distribution of fluorescence values demonstrates that the microspheres are randomly positioned in the sample stream.

In comparison, FIG. 17b graphically shows acoustic radiation pressure provided by the present invention aligning the subject fluorescent microspheres within the fluid stream, ensuring that all microspheres experience uniform illumination. FIG. 17b shows this in that the distribution of fluorescence intensities forms a tight peak, indicating that the microspheres are excited with similar intensities of focused laser light. This result demonstrates that acoustic radiation pressure can be used to align analytes into a sample core similar in fashion to hydrodynamic focusing used in prior art flow cytometers.

Furthermore, as the present invention both focuses and concentrates analytes; it is possible to analyze high numbers of analytes at low linear velocities. For example, a volumetric sample delivery rate of 75 µl/minute through a 200 µm diameter channel yields a core velocity (2× average velocity) of 8 cm/s. This is much slower than a traditionally focused flow cytometer (usually in the 1 m/s to 10 m/s range). Thus, use of the present invention yields a transit time of about 250 µs through a 20 µm interrogation volume. This slow transit time (~20 to 100 times slower than conventional systems) allows for analyte analysis rates using lower speed data acquisition systems that are less expensive, smaller, and that require less power. The extended transit time provided by the present invention allows for longer collection of optical signals that provide higher sensitivity measurements than conventional systems.

Additionally, the concentration effect of acoustic focusing allows for the analysis of very dilute samples that would be difficult to analyze due to time constraints using conventional flow cytometry systems. For example, using a large diameter focusing chamber, samples can be delivered at ml/minute volumetric flow rates. This is a very high sample delivery rate compared to most conventional hydrodynamic flow systems (μl/minute), which enables the analysis of highly dilute samples commonly found in bioforensics and other applications. By increasing the diameter of the flow chamber even more dilute samples can be effectively analyzed. In fact, the diameter of the focusing chamber may be tailored to fit the expected concentration of the samples to be analyzed.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for concentrating analyte within a fluid using acoustic radiation pressure, said apparatus comprising:
    a function generator to output a radiofrequency electrical signal;
    a single acoustic signal producing transducer; and
        a tube comprising an inherently axially symmetric geometry;
        said single acoustic signal producing transducer acoustically coupled to said tube and used to transform said radiofrequency electrical signal to an acoustic signal;
        said tube converting said acoustic signal to said acoustic radiation pressure within said tube, and said acoustic pressure concentrating the analytes within said tube.

2. The apparatus of claim 1 wherein said tube comprises an elastic material.

3. The apparatus of claim 1 wherein said geometry of said driving transducer is cylindrical.

4. The apparatus of claim 1 wherein said function generator is selected from any voltage source circuit capable of producing a variety of voltage waveforms of varying frequencies.

5. The apparatus of claim 1 further including a power amplifier to amplify said output of said function generator.

6. The apparatus of claim 1 further including a monitoring transducer to monitor said acoustic radiation pressure to maintain resonant frequency and compensate for ambient temperature fluctuations.

7. The apparatus of claim 6 wherein said second transducer is selected from the group consisting of piezoceramic, piezosalt, piezopolymer, piezocrystal, magnetostrictive, and electromagnetic transducers.

8. A method for concentrating analyte within a fluid using acoustic radiation pressure, the method comprising:
    producing the acoustic radiation pressure in a tube comprising an inherently axially symmetric geometry using a single acoustic signal producing transducer;
    flowing a fluid with the analyte through the tube;
    driving the transducer and inducing an outer boundary surface displacement; and
    concentrating the analyte within the tube.

9. The method of claim 8 further including:
    monitoring the outer boundary surface displacement;
    and adjusting the acoustic radiation pressure to maintain a resonant frequency and adjust for ambient temperature changes via a monitoring transducer.

10. A flow cytometer for the analysis of analytes, comprising:
    a tube having an inlet for accepting a fluid sample stream of the analytes;
    an acoustic signal producing transducer coupled to said tube, wherein said acoustic signal producing transducer produces an acoustic signal to said tube to induce within said tube acoustic radiation pressure capable inducing an outer boundary surface displacement to concentrate the analytes within the fluid sample stream;
    optical equipment for analyzing the analytes wherein said optical equipment comprises a light source to create light scatter along with several wavelength bands of fluorescence for analyzing the analytes; and
    collection optics to receive the light scatter and the several wavelength bands of fluorescence created to determine molecular makeup of the analytes.

11. The flow cytometer of claim 10 wherein said tube comprises an inherently axially symmetric geometry.

12. The flow cytometer of claim 10 wherein said tube is cylindrical.

13. The flow cytometer of claim 10 wherein said function generator is selected from any voltage source circuit capable of producing a variety of voltage waveforms of varying frequencies.

14. The flow cytometer of claim 10 further including a power amplifier to amplify the output of said function generator.

15. The flow cytometer of claim 10 further including a monitoring transducer to monitor the acoustic radiation pressure to maintain resonant frequency and compensate for ambient temperature fluctuations.

16. The flow cytometer of claim 15 wherein said monitoring transducer is selected from the group consisting of piezoceramic, piezosalt, piezopolymer, piezocrystal, magnetostrictive, and/or electromagnetic transducers.

17. The flow cytometer of claim 10 wherein said light source is a laser.

18. The flow cytometer of claim 10 wherein said light source is an arc lamp.

19. A method of flow cytometry, comprising:
    supplying a fluid stream with analytes to an inlet of a tube;
    subjecting the tube to acoustic radiation pressure to induce an outer boundary surface displacement to concentrate the analytes within the fluid stream; and
    analyzing the analytes via a flow cytometer.

20. The method of claim 19 further comprising monitoring the outer boundary surface displacement and adjusting the acoustic radiation pressure to maintain a resonant frequency and adjust for ambient temperature changes.

21. A method of flow cytometry comprising:
    supplying a fluid stream with analytes to an inlet of a tube;
    subjecting the tube to acoustic radiation pressure to induce an outer boundary surface displacement to concentrate the analytes within the fluid stream; and
    analyzing the analytes with optical equipment, wherein analyzing the analytes includes subjecting the analytes to a light source that creates light scatter and several bands of fluorescence, and collecting the light scatter and wavelength bands of fluorescence with an optical detector, and identifying the collected wavelength bands to determine molecular makeup of the analytes.

22. The method of claim 21 wherein analyzing the analytes comprises collecting magnetic moment signals and determining the molecular makeup of the analytes.

23. A flow cytometer for analysis of analytes comprising:
    a tube having an inlet for accepting a fluid stream with analytes;

a single acoustic signal producing transducer acoustically coupled to said tube;

said single driving transducer producing an acoustic signal that induces acoustic radiation pressure in said tube to produce an outer boundary surface displacement to concentrate the analytes within the fluid stream; and a flow cytometer fluidly connected to said tube for analyzing the analytes.

24. The flow cytometer of claim 23 further comprising a monitoring transducer for monitoring said outer boundary surface displacement, and adjusting said acoustic radiation pressure to maintain a resonant frequency and adjust for ambient temperature changes.

25. The flow cytometer of claim 23 wherein said tube comprises an inherently axially symmetric geometry.

26. The flow cytometer of claim 25 wherein said tube comprises a cylindrical shape.

* * * * *